United States Patent [19]

Cunningham

[11] Patent Number: 5,002,529
[45] Date of Patent: Mar. 26, 1991

[54] POSTOPERATIVE WOUND DRAINAGE

[75] Inventor: Robert W. Cunningham, Cohasset, Mass.

[73] Assignee: Solco Basle, Inc., Hingham, Mass.

[21] Appl. No.: 72,224

[22] Filed: Jul. 10, 1987

[51] Int. Cl.$^5$ .............................. A61M 1/06
[52] U.S. Cl. ........................... 604/73; 604/35; 604/319; 604/27; 604/4; 604/408
[58] Field of Search ............... 604/19, 21, 27, 28, 604/29, 35, 73, 317, 319, 322, 408, 4, 5, 6

[56] References Cited

U.S. PATENT DOCUMENTS

| | | | |
|---|---|---|---|
| 2,700,973 | 2/1955 | Ju | 604/317 |
| 3,648,698 | 3/1972 | Doherty | 604/319 |
| 4,397,643 | 8/1983 | Rygiel | 604/317 |
| 4,402,687 | 9/1983 | Denty et al. | 604/319 |
| 4,437,856 | 3/1984 | Valli | 604/29 |
| 4,516,973 | 5/1985 | Telang | 604/319 |
| 4,573,992 | 3/1986 | Marx | 604/408 |
| 4,675,010 | 6/1987 | Siposs et al. | 604/319 |
| 4,681,564 | 7/1987 | Landreneau | 604/29 |
| 4,767,417 | 8/1988 | Boehringer et al. | 604/31 |
| 4,781,707 | 11/1988 | Boehringer et al. | 604/317 |

FOREIGN PATENT DOCUMENTS

| | | | |
|---|---|---|---|
| 1947123 | 3/1970 | Fed. Rep. of Germany | 604/317 |
| 3410163 | 9/1985 | Fed. Rep. of Germany | 604/319 |
| 3523843 | 1/1987 | Fed. Rep. of Germany | 604/319 |

Primary Examiner—C. Fred Rosenbaum
Assistant Examiner—Kathleen A. Daley
Attorney, Agent, or Firm—Donald Brown

[57] ABSTRACT

A system and method for draining a postoperative wound, the system having a bottle which is coupled in a manner to facilitate fill of the bottle under low pressure from a postoperative wound.

2 Claims, 1 Drawing Sheet

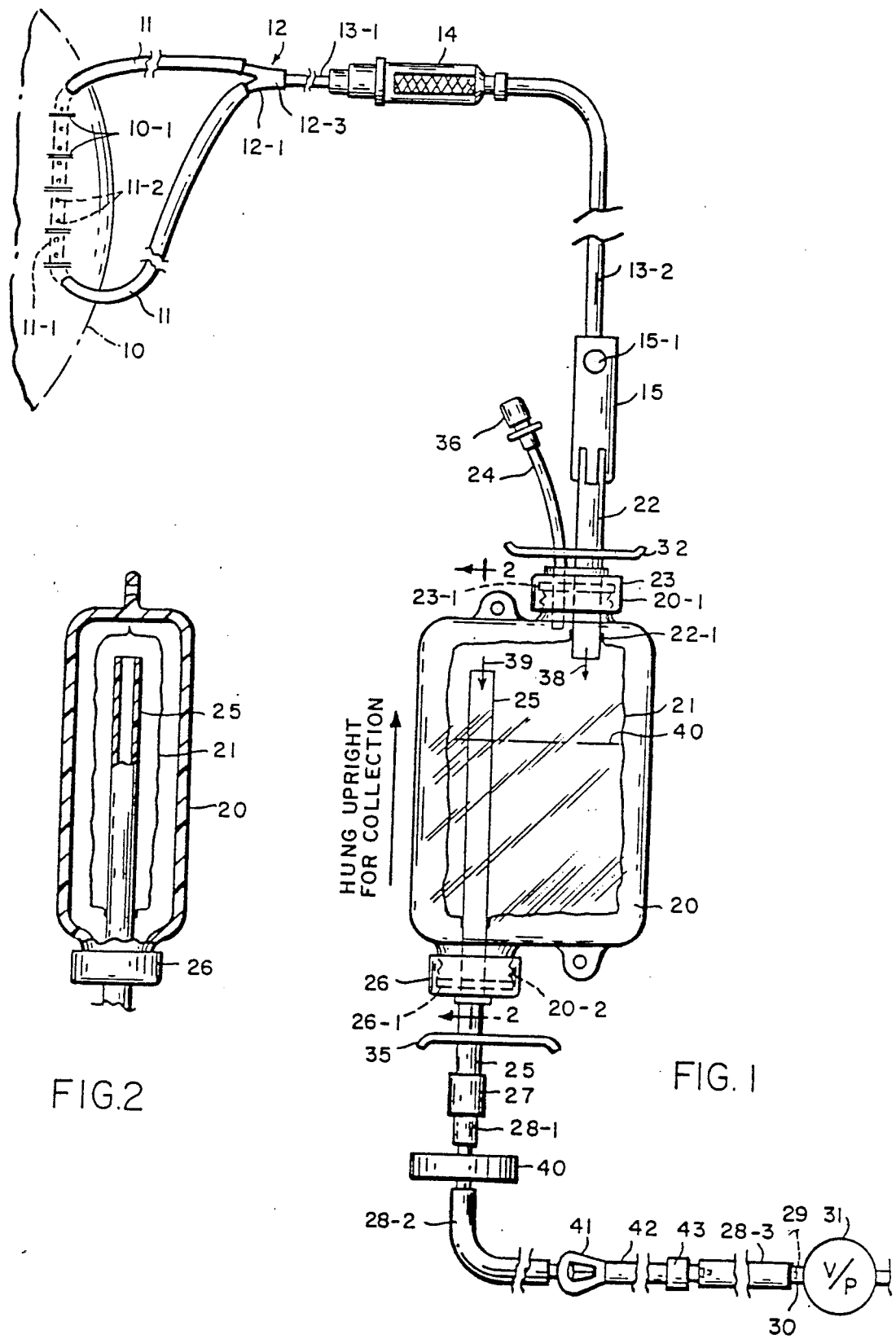

POSTOPERATIVE WOUND DRAINAGE

BACKGROUND OF THE INVENTION

This invention is directed to a new system and method for closed wound draining e.g., the type of wound which occurs during surgery and is subsequently sewn or closed and then drained of fluid after surgery.

More particulary, the present invention is directed to the use of an auto-infusion bottle or container sold under the trademark SOLCOTRANS by Solco Basle, Inc. of Rockland, Mass, U.S.A., and which is normally used for intraoperative auto-transfusion (i.e., the collection of blood during surgery and thereafter the transfusion of the patient with the same collected blood) for postoperative wound drainage. When one uses the Solcontrans TM bottle for intraoperative auto-transfusion, collected blood feeds into the inner bag in the bottle via a elongated fill tube against gravity and then falls into an inner bag. Thus collected debris e.g., bone collected with the blood from the surgical incision area is not able to clog the inlet fill tube for collecting the blood.

However, the use of the Solcotrans TM bottle in this manner has not been found satisfactory when used in conjunction with postoperative closed wound drainage catheters because the blood which is sucked into the fill tube is evacuated at low pressure has to flow against the hydrostatic pressure head generated by the height of the fill tube thereof.

The present invention provides a solution to using the Solcotrans TM bottle for closed wound drainage.

BRIEF DESCRIPTION OF THE INVENTION

In this invention, a Solcotrans TM bottle is coupled to a closed wound drainage catheter through a Y connector by way of a pre-filter and connector to a port of the Solcotrans TM bottle which goes directly into the inner bag contained within the semirigid outer bottle thereof and the port connected to the fill tube of the Solcotrans TM bottle is coupled through a vacuum tube assembly to a low-pressure source of suction or none if one wants to rely upon gravity flow. It is therefore now possible to use the Solcotrans TM bottle at low pressures from 0 mm Hg (gravity flow) to about 80 mm Hg (negative pressure) for postoperative wound drainage and therefore improve flow rates, prevent clotting in the fill tube and improve admixture of blood with the anticoagulant solution placed in the bag. Reference may be had to U.S. Pat. No. 4,573,992 to show the state of the art.

BRIEF DESCRIPTION OF THE DRAWING

FIG. 1 is a diagramatic view of the system of this invention for draining blood for a closed wound.

FIG. 2 is a sectional view taken along line 2—2 of FIG. 1.

DETAILED DESCRIPTION OF THE INVENTION

Reference should now be had to FIGS. 1 and 2 for a descriptiion of the system of the invention.

At 10, there is shown a portion of a patient e.g., a human having a wound 10-1. Placed within the wound is a wound drainage catheter 11 i.e., for draining blood, having a section 11-1 with a plurality of holes 11-2 for draining the wound. The section 11-1 is placed into the wound and the skin is punctured or sewn together to hold the catheter section 11-1 therein. Coupled to the ends 11-3 and 11-4 of the catherer 11 is a Y connector 12 having the top Y sections 12-1 and 12-2 coupled to opposite ends of the catheter. The Y section 12-3 is connected to a blood collection tube 13-1 and then preferably to a typical pre-filter 14 to tube 13-2 which in turn is coupled to a connector 15 which has a sterile rubber sealed injection port 15-1 to inject anticoagulant and etc. At 20, there is disclosed the conventional SOLCOTRANS brand auto-transfusion device which comprises a semirigid plastic bottle 20 having an inner flexible plastic bag 21, positioned in the bottle 20. At one end of the bag a tube 22 forms a port for the collection of blood. The tube 22 extends into the bag a small distance sufficient to allow bag to tube sealing e.g., less than ¼ the length of the bag towards the opposite end into the bag 21 and is sealed therein at 22-1. The tube 22 extends through a cap 23 having a sealing washer 23-1 attached to the tube 22 which adapted to be forced down on a threaded neck portion 20-1 by the cap 23. Also extending into the sealing cap 20-1 through the sealing washer 23-1 is tube 24 for providing gas under pressure between the inner bag and the outer bottle to cause the bag 21 to expel blood contained therein if it desired to return the collected blood to the human patient. A fill tube is shown at 25 at the bag end opposite tube 23 and forms a second port. The tube 25 extends more than halfway and preferably at least 9/10 of the distance towards the bag end coupled to said first port formed by tube 22. The tube 25 is sealed into the bag 21 and the portion thereof extends through a sealing cap 26 coupled to a threaded neck portion 20-2 through a sealing washed 26-1. The sealing washer 26-1 is sealed about tube 25 is forced against the top of the neck portion 20-2 by the cap 26.

The tube 25 is connected to a connector 27, which is preferably coupled to a vacuum tube assembly through a tube 28-1, a 0.2–0.5 micron filter 40 (to provide for bacterial filtering), a tube 28-2, a one-way check valve 41 (e.g., a Duckbill valve to allow for air to be drawn out of the bag 21 but no air flow into the bag 21) and a tube 42 and a connector 43 coupled to a tube 28-3. The vacuum tube assembly comprises a tube 28-3 (as noted), connector 29, tube 30 which is coupled if desired to a vacuum pump 31 to provide suction unless gravity fill is being used. In use, the pump is generally used at low-pressure suction under 80 mm Hg negative pressure to suck blood from the wound through the pre-filter and then into the bottle to fill levels below the top of the fill tube.

Conventional slideable clips having a narrowed portion are provided at 32 and 35 for closing the tubes 22 and 25 if desired and a cap 36 is provided to close tube 24. The arrow 38 at tube 22 represents the flow of blood into the bag which is collected to the level represented by the dotted line 40 and the arrow 39 represents air flow due to the suction pump 31.

During filling of the bag 21, it is held upright vertical (fill tube 25 below tube 22 outlet) as shown in FIG. 1. The fitler 14 may be purchased from e.g., Bipore Inc. of Demarest N.J., the 0.2 to 0.5 micron filter 40 may be purchased from e.g., Filtertech Corporation of Hebron, Illinois and the Duckbill valve 41 may be purchased from e.g., Cutter Biologicals, Emeryville, Calif.

In the drawing, the plastic of the outer container 20 is transparent so that the inner bag 21 and tubes can be seen.

I claim:

1. A system for draining blood from a post-operative closed wound and then capable of providing blood therefrom to be reused by the patient comprising a closed wound drainage catheter connector coupled to a first tube, said first tube coupled to the first end of a flexible bag, said first tube extending into said bag less than ¼ the length of said bag towards the second end of said bag, and first tube being for blood collection and capable of subsequent blood flow from said bag, a second tube coupled to the flexible bag at the second end of said bag and extending at least half the length of said flexible bag towards the first end of the bag, said first tube extending a distance towards the second end of the flexible bag less than the distance of the second tube from said first end of said flexible bag, a bacterial air filter coupled to said second tube, a one way valve coupled to said second tube to prevent air from entering said bag from second tube but to allow air flow out of said bag through said second tube, and a semirigid outer shell enclosing said flexible bag and surrounding a portion of each of said first and second tubes.

2. A method for draining blood for a post-operative closed wound of a patient which then can be reused in the patient, which comprises placing a closed wound catheter in the wound of a patient and closing the wound about the catheter portion having holes therein for collecting blood, said closed wound catheter coupled to a first tube, said first tube coupled to the first end of a flexible bag, said first tube extending into said bag less than ¼ the length of said bag towards a second end of said bag, a second tube coupled to second end of said bag and extending at least half the length of said flexible bag towards the first end of the bag, said first tube extending a distance towards the second end of the flexible bag less than the distance of the second tube form said first end of said flexible bag, a bacterial air filter coupled to said second tube and a semirigid outer shell enclosing said flexible bag and surrounding a portion of each of said first and second tubes placing the bag below the level of the wound to be drained, opening an air clamp coupled to said second tube to permit air to escape from the bag as blood is collected through said first tube.

* * * * *